(12) United States Patent
Matsuoka et al.

(10) Patent No.: US 8,867,818 B2
(45) Date of Patent: Oct. 21, 2014

(54) METHOD OF CREATING TEMPLATE FOR MATCHING, AS WELL AS DEVICE FOR CREATING TEMPLATE

(75) Inventors: Ryoichi Matsuoka, Yotsukaido (JP); Akiyuki Sugiyama, Hitachinaka (JP); Yasutaka Toyoda, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/387,382

(22) PCT Filed: Jul. 15, 2010

(86) PCT No.: PCT/JP2010/004588
§ 371 (c)(1),
(2), (4) Date: Jan. 27, 2012

(87) PCT Pub. No.: WO2011/013317
PCT Pub. Date: Feb. 3, 2011

(65) Prior Publication Data
US 2012/0121160 A1    May 17, 2012

(30) Foreign Application Priority Data
Jul. 31, 2009    (JP) .................................. 2009-178572

(51) Int. Cl.
*G06K 9/50* (2006.01)
*H01J 37/28* (2006.01)
*G01N 23/225* (2006.01)
*G06T 7/00* (2006.01)
*G06K 9/62* (2006.01)
*H01L 21/66* (2006.01)

(52) U.S. Cl.
CPC ................. *H01J 37/28* (2013.01); *H01L 22/12* (2013.01); *G06T 2207/30148* (2013.01); *G01N 23/225* (2013.01); *H01J 2237/221* (2013.01); *G06T 7/001* (2013.01); *H01J 2237/2817* (2013.01); *G06K 9/6255* (2013.01)
USPC ....................................................... 382/145

(58) Field of Classification Search
None
See application file for complete search history.

(56) References Cited

U.S. PATENT DOCUMENTS 6,904,164 B2    6/2005    Norioka et al.
7,615,746 B2   11/2009    Nagatomo et al.
(Continued)

FOREIGN PATENT DOCUMENTS

| JP | 6-34722 A | 2/1994 |
| JP | 11-251224 A | 9/1999 |

(Continued)

OTHER PUBLICATIONS

Japanese Office Action received in Japanese Application No. 2009-178572 dated Oct. 29, 2013.

*Primary Examiner* — Stephen R Koziol
*Assistant Examiner* — Delomia Gilliard
(74) *Attorney, Agent, or Firm* — Mattingly & Malur, PC

(57) ABSTRACT

Disclosed is a method wherein a template for template matching is created with high accuracy and high efficiency. With respect to each individual pattern constituting a basic circuit, pattern information regarding a plurality of layers in a semiconductor device is stored in a library. On the basis of the designation of the position and the layer, pattern information regarding the designated position and layer is extracted from the pattern information stored in the library. A template is created on the basis of the extracted pattern information.

12 Claims, 12 Drawing Sheets

(56) References Cited

U.S. PATENT DOCUMENTS

| | | |
|---|---|---|
| 7,732,792 B2 | 6/2010 | Matsuoka et al. |
| 2005/0076323 A1* | 4/2005 | Gau et al. ........................ 716/21 |
| 2007/0023653 A1* | 2/2007 | Toyoda et al. ................ 250/310 |
| 2009/0039261 A1* | 2/2009 | Toyoda et al. ................ 250/310 |
| 2009/0039263 A1* | 2/2009 | Matsuoka et al. ............ 250/311 |
| 2009/0087103 A1 | 4/2009 | Abe et al. |

FOREIGN PATENT DOCUMENTS

| | | |
|---|---|---|
| JP | 2002-50572 A | 2/2002 |
| JP | 2002-353280 A | 12/2002 |
| JP | 2006-351888 A | 12/2006 |
| JP | 2007-147366 A | 6/2007 |
| JP | 2009-043937 A | 2/2009 |
| JP | 2009-086920 A | 4/2009 |

* cited by examiner

METHOD OF CREATING TEMPLATE FOR MATCHING, AS WELL AS DEVICE FOR CREATING TEMPLATE

TECHNICAL FIELD

The present invention relates to a method, device, and program for creating a template for template matching and, more particularly, to a method, device, and computer program for creating a template based on pattern information registered as a library.

BACKGROUND ART

In recent years, in inspection of semiconductor devices and masks, various metrology techniques using design data (layout patterns) created for semiconductor manufacturing have been proposed and have become to be used in measurements and so on of semiconductor devices relying on a scanning electron microscope (SEM).

In particular, patent literature 1 explains a technique for performing pattern matching between a line segment based on design data and a pattern image obtained by a scanning electron microscope and measuring a pattern identified by the pattern matching. More specifically, a reference image called a template is created on the basis of design data. The template and an electron microscope image are compared to thereby find the degree of match. A position at which there is a high degree of match is identified as a matching position.

Furthermore, a technique in which either a forecasted shape pattern of a transferred pattern obtained by simulating the exposure of the semiconductor process using design data or a pattern deformed by image processing is used for pattern recognition is proposed in patent literature 1.

Patent literature 2 explains a technique of previously obtaining an SEM image and turning the image into a template in order to create the template.

CITATION LIST

Patent Literatures

Patent literature 1: JP-A-2007-147366
Patent literature 2: JP-A-2009-86920

SUMMARY OF INVENTION

Technical Problem

The technique of creating a template close to an actual image (SEM image) using a simulation or image processing as disclosed in patent literature 1 can create an appropriate template in a case where the conditions of the simulation or image processing are appropriate but it takes a considerable time to adjust the simulation conditions or to perform the simulation itself. Furthermore, in a case where it is difficult to find optimum simulation conditions, it is difficult to create an appropriate template.

In the method of creating a template on the basis of an actual image as disclosed in patent literature 2, it is possible to create a template faithful to the actual image but it is necessary to obtain, through the use of an SEM or the like, an image of a sample to be inspected. Furthermore, it is necessary to derive an SEM image whenever the magnification or the like of the obtained image varies, thus requiring considerable labor.

A method, device, and computer program intended to create a template for template matching at high accuracy and high efficiency is hereinafter described.

Solution to Problem

As one aspect for achieving the above-described object, a method and a computer program are proposed which store pattern information about plural layers of a semiconductor device as a library for each pattern forming a basic circuit, extract pattern information from the library based on designation of a position, and create a template for template matching on the basis of the pattern information. Furthermore, as another aspect, a template creating device having a storage medium on which the library is stored is proposed.

Advantageous Effect of Invention

According to the above-described configuration, it is possible to provide method, device, and computer program for creating a template for template matching at high accuracy and high efficiency.

DESCRIPTION OF EMBODIMENTS

Figure 1:
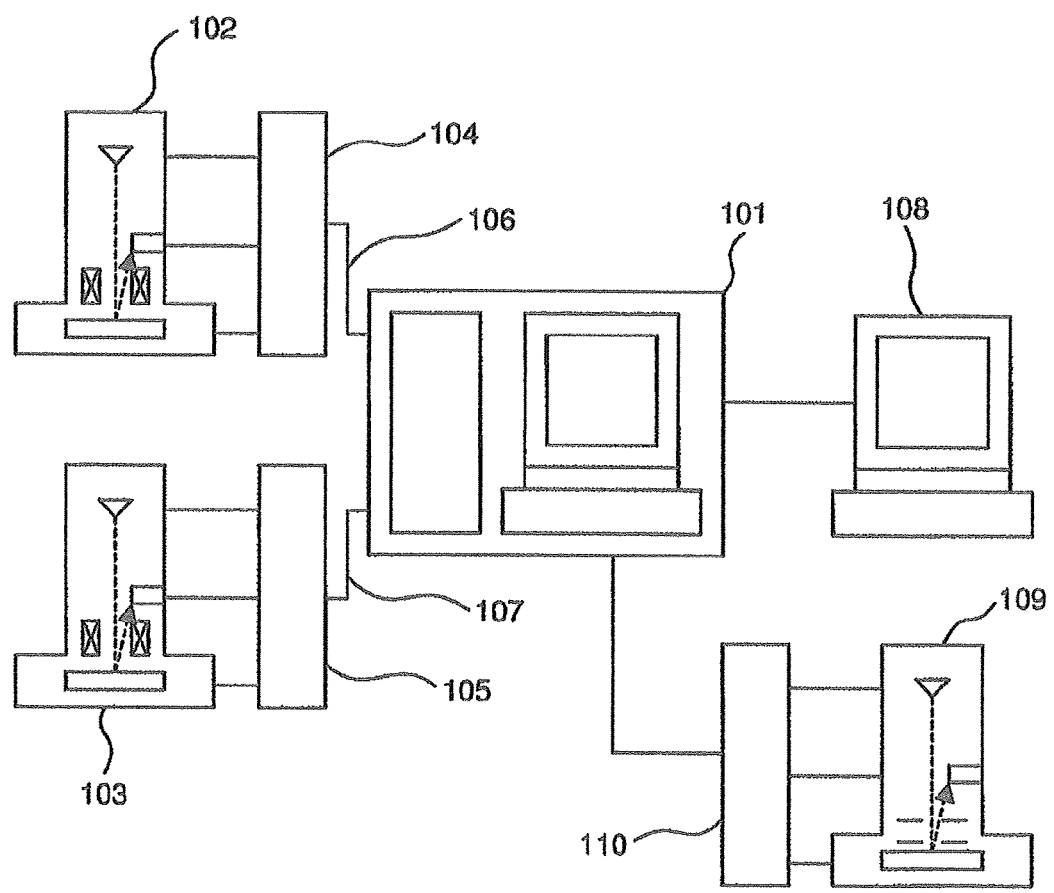
FIG. 1 is a diagram schematically illustrating a measurement system including plural measuring instruments.

These days, in inspection of semiconductor devices and masks, various measurement techniques using design data (layout pattern) created for semiconductor manufacturing are proposed and have begun to be used in measurements and so on of semiconductor devices utilizing scanning electron microscopes (SEMs).

As a principal technical field, an example has been published in which pattern matching is performed between a line segment based on design data and a contour line of a pattern obtained by a scanning electron microscope and in which the pattern identified by the pattern matching is measured.

In particular, design data is used in pattern matching for precisely recognizing a target pattern for a measurement. A semiconductor pattern and a mask to be measured are precisely recognized. Thus, labor required to create a measurement recipe that is a preparatory work for a measurement is reduced.

Furthermore, by making measurements using images associated with design data, good effects are produced in applications other than metrology (length measurements) such as OPC modeling, verification, and decisions and evaluations on hot spots (dangerous locations).

The method of reducing labor in creating a recipe by using design data in pattern recognition has the following point at issue. Generally, a pattern shape of semiconductor fabricated by microlithography is fabricated as a shape deviating from the design shape by the effects of exposure characteristics and by the effects of a process control in an etching step. There is a possibility that misrecognition or the like might occur during pattern recognition, creating a factor hindering automation of inspections and measurements. This is one factor deteriorating the productivity.

On the other hand, as one means for improving the accuracy of these pattern recognitions, a technique consisting of simulating exposure of the semiconductor process using design data and using the thereby forecasted shape of the transferred pattern in pattern recognition is proposed.

Although the present method improves the pattern recognition accuracy in some cases, optimum parameter adjustments for simulation during a preparatory work in creating a recipe and the work time for execution of the simulation are problematic.

In addition, even if a simulated shape is used, it is difficult to obtain a simulated shape that faithfully reflects the transferred shape due to parameters of the scanner used for exposure of the pattern, variations between scanner machines, and variable factors of semiconductor processes. This is one factor causing misrecognition of pattern recognition.

Another available method consists of previously taking an SEM image for pattern recognition used heretofore and making a recipe for pattern recognition using the image. It is necessary to once take an image by a metrology instrument (SEM) using a wafer to be inspected. For ASIC's which are produced in small amounts but in many types, it is necessary to take an SEM image for creation of a recipe for each individual type. This is a factor hindering saving of labor and producing human errors.

Furthermore, such an SEM image can be used only at the same magnification as when the image was taken. Therefore, it cannot be used in measurements made at various magnifications. There is the weakness that the flexibility is low.

Method, device, and computer program (or storage medium on which the computer program is stored) capable of solving one or more of the foregoing problems are hereinafter described with reference to drawings. More particularly, a method of creating a recipe for a critical dimension-scanning electron microscope (CD-SEM) that is one type of measuring instrument is described.

Additionally, they can also be applied to equipment for detecting defects in a pattern, as well as to equipment for measuring the dimensions of a pattern. In the following description, an SEM is used as one form of charged particle beam instrument. The instrument is not restricted to the SEM. For example, a focused ion beam (FIB) system that forms an image by scanning an ion beam over a sample may be adopted as a charged particle beam instrument. In order to accurately measure patterns manufactured with ever decreasing dimensions, quite high magnification is required and so it is generally desired to use SEMs because they are superior in resolution than FIB systems.

FIG. 1 exemplifies a system including a data management unit 101 as its main component as well as plural SEMs connected with the management unit. Especially, in the case of the present embodiment, an SEM 102 is mainly intended to measure and inspect patterns of a photomask and recticles used in semiconductor exposure processes. An SEM 103 is mainly used to measure and inspect a pattern transferred onto a semiconductor wafer by exposure using the photomask or the like. The SEM 102 and SEM 103 are not greatly different in fundamental structure of electron microscope but are configured to cope with variations in size between semiconductor wafer and photomask and with different resistances to electrical charging.

Controllers 104 and 105 are connected with the SEMs 102 and 103, respectively, to provide control necessary for the SEMs. In each SEM, an electron beam emitted from an electron source is focused by plural stages of lenses. The focused electron beam is scanned over the sample in one or two dimensions by a scan deflector.

Secondary electrons (SE) or backscattered electrons (BSE) released from the sample in response to the electron beam scanning are detected by a detector and stored on a storage medium such as a frame memory in synchronism with the scanning made by the scan deflector. The scanning by the scan deflector can be made for arbitrary size, position, and direction. This permits scanning for forming an image as described later and selective scanning of edge portions.

The control and so on described so far are provided by the controllers 104 and 105 for the SEMs. Images and signals obtained as a result of the electron beam scanning are sent to the data management unit 101 via communication lines 106 and 107. In the description of the present embodiment, the controllers controlling the SEMs are separate from the data management unit that makes measurements based on signals obtained by the SEMs. The invention is not limited to this. The data management unit may perform both control of an instrument and processing for measurements. Each of the controllers may perform both control of the SEM and processing for measurements.

The data management unit or each controller is loaded with a program for executing the processing for measurements. Measurements or calculations are performed in accordance with the program. Furthermore, a design data management device is loaded with design data for photomasks (hereinafter may be simply referred to as masks) and for wafers used in semiconductor manufacturing steps. The design data is expressed, for example, in GDS format or OASIS format and stored in a given format. Any type of design data can be used as long as software that displays the design data can display its format and treat the data as graphical data. In addition, the design data may be stored on a storage medium separate from the data management unit.

A simulator 108 is connected with the data management unit 101. The simulator 108 is loaded with a program for creating a pattern layout based on design data stored on an external storage medium or in the data management unit 101 and on semiconductor manufacturing process conditions or the like. The simulator incorporates an arithmetic unit for executing the program. Layout data obtained after the simulation can be transferred to the data management unit. In the description of the present embodiment, an example in which the simulation is performed within the simulator 108 is given.

The invention is not restricted to this. Alternatively, a simulation may be performed by executing the program, for example, within the data management unit 1.

Furthermore, the data management unit 101 is equipped with a function of creating a program (recipe) for controlling the operation of the SEMs based on the design data about the semiconductor, and acts also as a recipe setting portion. In particular, the data management unit creates a program for setting desired measurement points, positions or the like at which processing necessary for the SEM is set such as autofocus, auto stigmator, addressing, or the like using only design data, contour line data about a pattern, or simulated design data, and for automatically controlling the SEM sample stage, deflectors, and so on based on the settings.

As described later, a database for a pattern library for basic devices is stored in the data management unit 1, which is so configured that necessary data is read from the database according to any arbitrary settings.

A template matching process using a reference image known as a template is a technique for identifying locations where degrees of match with the template are highest or in excess of a given value within a search area that is searched for desired locations by moving the template through the search area. The controllers 104 and 105 carry out pattern matching based on a template that is one item of information registered in the recipe.

As exemplified in FIG. 1, a focused ion beam system 109 for directing helium ions, liquid metal ions, or the like at the sample and its controller 110 may be connected with the data management unit 101. The data management unit 101 may be used for creation of a measurement recipe for the focused ion beam instrument 109, measurements, and management of the results of machining.

Figure 2:
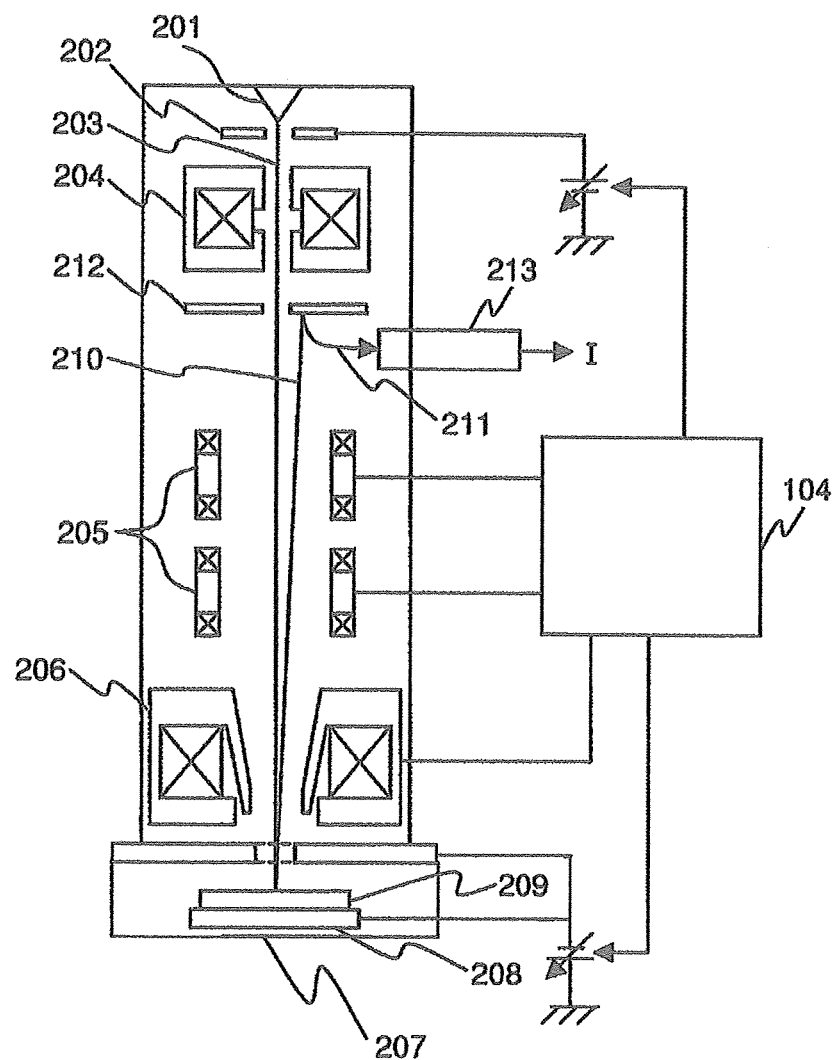
FIG. 2 is a schematic block diagram of a scanning electron microscope.

FIG. 2 is a schematic block diagram of a scanning electron microscope. An electron beam 203 extracted from an electron source 201 by an extraction electrode 202 and accelerated by an acceleration electrode (not shown) is focused by a condenser lens 204 that is one form of focusing lens and then scanned over a sample 209 in one or two dimensions by a scan deflector 205. The electron beam 203 is decelerated by a negative voltage applied to an electrode included in a sample stage 208 and focused onto the sample 209 by the lens action of an objective lens 206.

When the electron beam 203 is made to impinge on the sample 209, electrons 210 such as secondary electrons and backscattered electrons are released from this irradiated portion. The released electrons 210 are accelerated toward the electron source by an accelerating action based on the negative voltage applied to the sample. The electrons collide with a conversion electrode 212, producing secondary electrons 211. The secondary electrons 211 released from the conversion electrode 212 are captured by a detector 213. The output I from the detector 213 varies depending on the amount of captured secondary electrons. The brightness of a display device (not shown) varies according to the output I. For example, where a two-dimensional image is formed, an image of the scanned region is formed by synchronizing a deflection signal fed to the scan deflector 205 and the output I from the detector 213.

In the description of the example of FIG. 2, electrons released from the sample are once converted by the conversion electrode and then detected. Of course, the invention is not restricted to this configuration. For example, the sensitive surface of an electron multiplier or detector may be so configured as to be disposed in the orbit of the accelerated electrons.

The controller 104 controls the various configurations of the scanning electron microscope and has a function of forming an image on the basis of the detected electrons and a function of measuring the pattern width of a pattern formed on the sample on the basis of the intensity distribution of detected electrons, known as a line profile.

Figure 3:
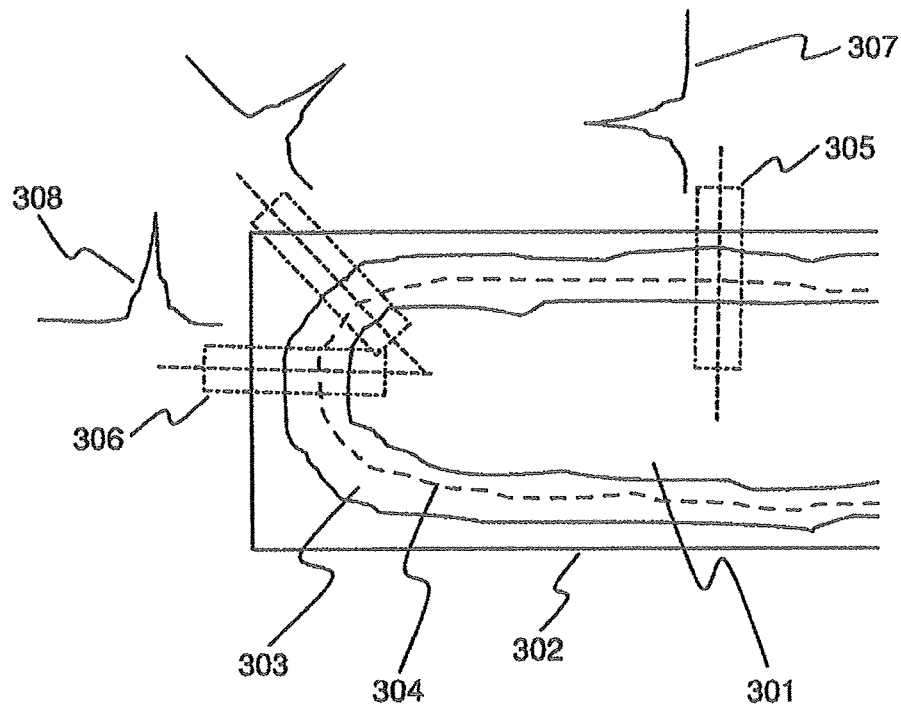
FIG. 3 is a diagram illustrating a method of extracting a contour line of a pattern image.
Figure 4:
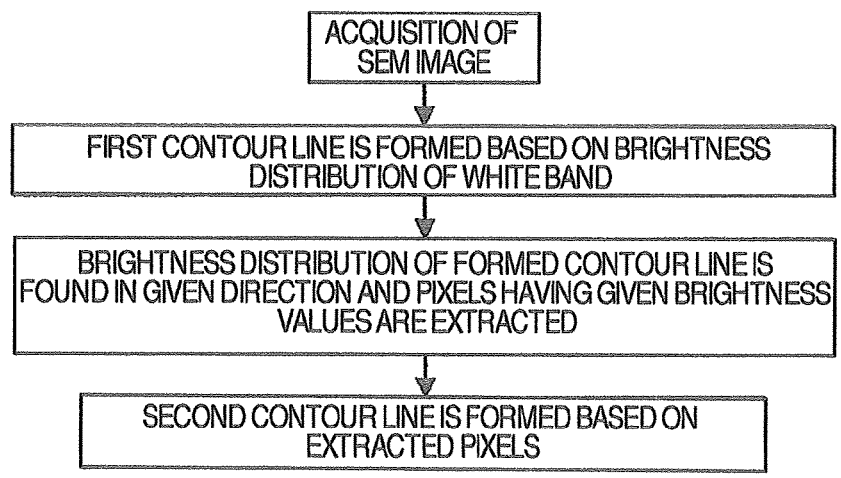
FIG. 4 is a flowchart illustrating steps for extracting a contour line from a pattern image.

FIG. 3 is a diagram illustrating one example of technique of extracting a contour line from a pattern image formed on the basis of the detected electrons. This step of extracting the contour line may be carried out by the arithmetic unit incorporated in the data management unit 101 or by the controllers 104 and 105 connected with the SEM. As exemplified in the flowchart of FIG. 4, in order to extract the contour line, an SEM image is first formed by the SEM 104 or SEM 105. Then, a first contour line 304 is extracted from a white band 303 corresponding to an edge portion of the pattern 301 on the SEM image. A conceivable method of extracting the first contour line 303 consists of extracting a pattern image composed of bitmap data from the SEM image and converting the pattern image into pattern data composed of vector data.

Then, layout data 302 and the first contour line 304 are made to overlap each other by comparing the formed first contour line 304 and the layout data 302 in terms of their vector data or performing pattern matching. The layout data 302 is information about line segments of design data stored in GDS format or the like. After making such overlapping, a region from which information about a brightness distribution is collected is set perpendicularly to the first contour line 304, and brightness distributions 307 and 308 are detected. A contour line can be formed more correctly by extracting pixels having a given brightness from the brightness distribution formed in this way and defining the position as a position of a second contour line. Existing techniques as described, for example, in JP-A-60-169977, JP-A-6-325176, JP-A-8-161508, and JP-A-9-204529 can be employed as such a precise method of forming a contour line.

The layout data and the first contour line can be correlated with each other one line segment at a time by overlapping the first contour line and the layout data as described previously. The contour line data can be registered in the same given format as the design data by making line segment information about each line segment possessed by the layout data each piece of line segment information about a contour line.

A method of efficiently creating templates used for template matching during measurements and inspections of semiconductor devices based on a basic circuit (basic elements) is described below.

A basic element is equivalent to a circuit performing a basic logic operation (such as a NAND) or a logic circuit (such as a sequential circuit). It is considered that plural basic elements are present on a semiconductor device. A semiconductor circuit pattern is mainly realized by a combination of basic circuits (such as transistors, inverters, NANDs, and so on).

During semiconductor manufacturing based on a technique of designing semiconductors, called the standard cell method, standard (basic) circuit cells providing a basis of a circuit are created prior to design of a semiconductor becoming a finished product. The unit of the circuit corresponds to a basic element of a signal processing circuit known as a logic gate such as a transistor (P type, N type, or the like), an inverter circuit, or a NAND circuit. it can be considered that each unit is a part taking account of electrical performance during the semiconductor manufacturing steps.

In designing and manufacturing a semiconductor becoming a finished product, a desired finished product of circuit is accomplished by combining these basic circuits as standard parts. This method is known as the standard cell method. A library of these basic circuit patterns is termed a standard cell library.

With respect to semiconductor circuits manufactured as finished products as described previously, a complex circuit of high level of integration is realized by combining these basic circuits. In the design and setup stage of semiconductor, circuits of the above-described basic circuits are designed, a mask is created, a pattern is formed on silicon, the transferability of the pattern is evaluated, and the validity of the circuit characteristics is verified.

The present embodiment pertains to measurements and inspections of semiconductor devices manufactured by application of the standard cell method that designs and manufactures semiconductor circuits after standardizing many basic circuit patterns present within a semiconductor circuit (turning them into a library). A technique capable of efficiently creating a template used especially during measurement or inspection is described.

In one form of the present embodiment, the shapes of transferred patterns of various basic circuits (semiconductor manufacturing owing to the standard cell method) constituting semiconductor circuits are put into a library as matching templates that are previously placed in position for imaging and used for pattern recognition during inspection when circuits in the form of finished products are manufactured. The template library is stored in the data management unit 1, controllers 104 and 105, or other storage medium and used during creation of a recipe. The system shown in FIG. 1 is a measuring system including a library creating portion for creating a template for matching from a standard circuit pattern, a recipe creating portion for creating a recipe for measurement for each individual semiconductor product to be investigated, and a measuring portion for measuring the subject of measurement by control of the recipe created using the library.

Figure 5:
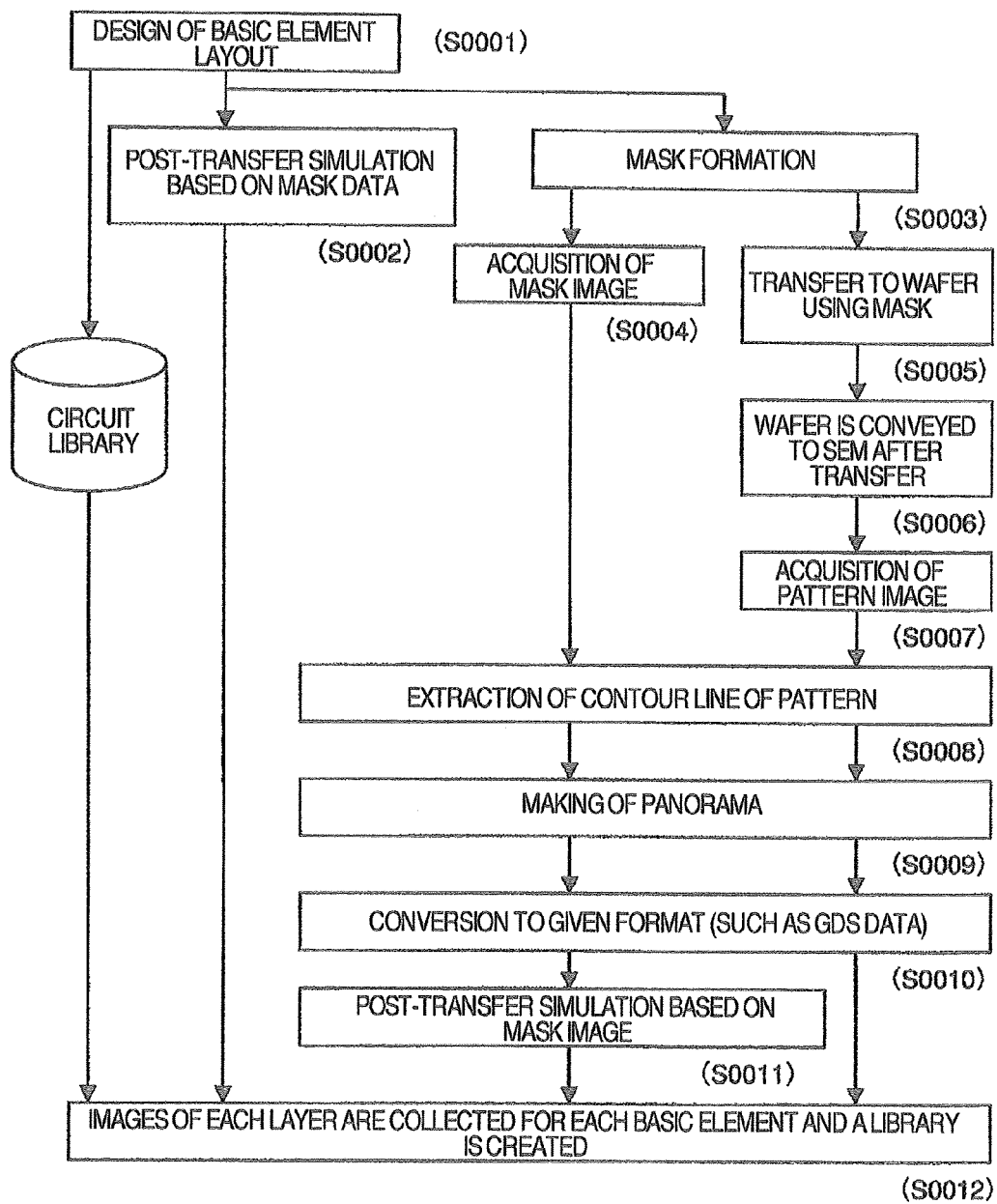
FIG. 5 is a flowchart illustrating steps for creating a template library used for template matching on the basis of basic circuit information.

FIG. 5 is a chart illustrating steps for creating a template library based on basic element information obtained by a design of a basic element layout. The following four steps are conceivable as steps for creating the template library on the basis of a library of the standard cell method obtained by a layout design (S0001) of basic elements.

Figure 13:
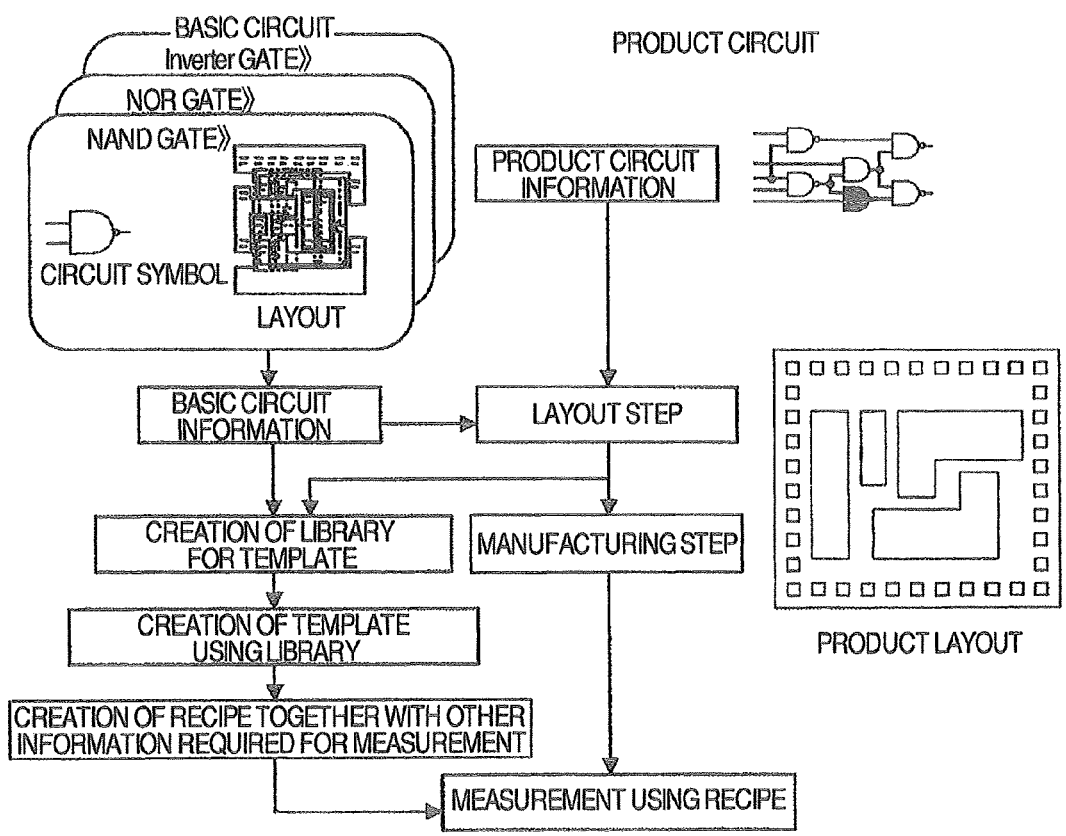
FIG. 13 is a flowchart illustrating steps for creating a measurement recipe based on a basic circuit design and steps for manufacturing circuits for products.

First, a technique for creating a template library by reading information stored in a standard cell library (circuit library) from a storage medium is described. In the present technique, the standard cell library stored on the storage medium is read out, for example, by the data management unit 1 and registered as a template library. FIG. 13 is a diagram illustrating steps for creating recipes for manufacturing and measurements of circuits in the form of finished products on the basis of the standard cell library (basic circuit information). In semiconductor design using the standard cell library, a layout of a pattern is designed on the basis of product circuit information in which plural basic circuits are combined and also on basic circuit information. At this time, the template library is created based on the basic circuit information. During the creation of the template library, information necessary when the recipe is created may be additively attached to assist subsequent creation of a recipe.

Figure 12:
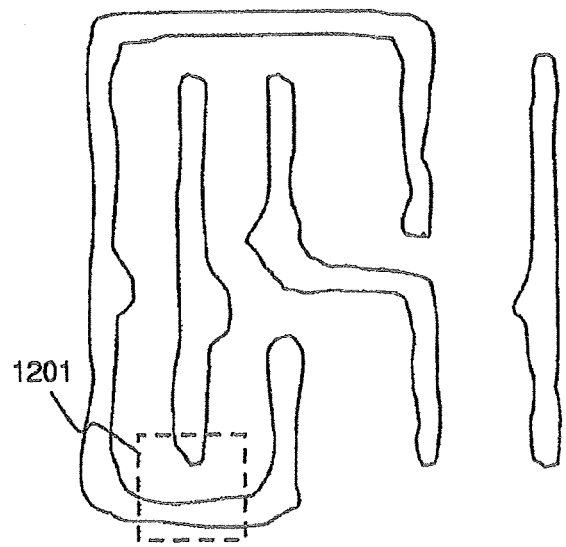
FIG. 12 is a view illustrating a step of selecting a region that is extracted as a template using only layout data.

Furthermore, during creation of the template library, processing may be performed to suppress deviation between thin lines of layout data and pattern edges to be matched, by simulating a post-transfer state for each layer by performing smoothing processing for each line segment of the layout data. The template is created on the basis of the template library created as described so far and on the layout data linked to the template library. Positions indicated by the layout data in which the basic circuits are arranged can also be stored in the template library. Based on positions indicated by the layout data or on designations of regions, basic circuits existing in the positions or in the regions are read out. Based on the information read out, the template is created. Regarding a template, an image becoming the template may be selected by selecting an arbitrary region indicated by the layout data for steps registered in the template library. A template region may be automatically determined on the basis of the selection of step names and measurement positions.

Where an arbitrary region is extracted as a template from among layout data of the template library, a template image is registered by selecting an arbitrary image region 1201 from among layout data about some step or from among contour line data, for example, as exemplified in FIG. 12.

Where the template region is automatically determined, an algorithm of searching the vicinities of the measurement position for a unique pattern on the basis of information about the measurement position may be applied. In this case, it is conceivable that a region having a unique shape will be selected as the pattern search region during pattern matching based on given decision criteria.

Since information regarding plural patterns existing on a sample is registered in the template library for each step, the recipe creator can easily carry out creation of a measurement recipe for an arbitrary step.

A recipe is created based on the template created as described so far and on other information necessary for the creation of the recipe. Using the recipe, a sample formed through manufacturing steps is measured. Where a transfer simulation of the layout data or approximation processing between the layout data and the pattern image using image processing is not performed, it is desired to perform such processing that template matching is performed in practice and then a region subjected to template matching is registered as a new template.

Then, a technique of creating a template library by carrying out a simulation of a post-transfer about the layout data or mask data (S0002) and creating the library on the basis of the results of the simulation is described. Since the post-transfer simulation results obtained by a simulation are the results of an estimation of the pattern obtained after a transfer, a library is created on the basis of the results (S0012).

Figure 8:
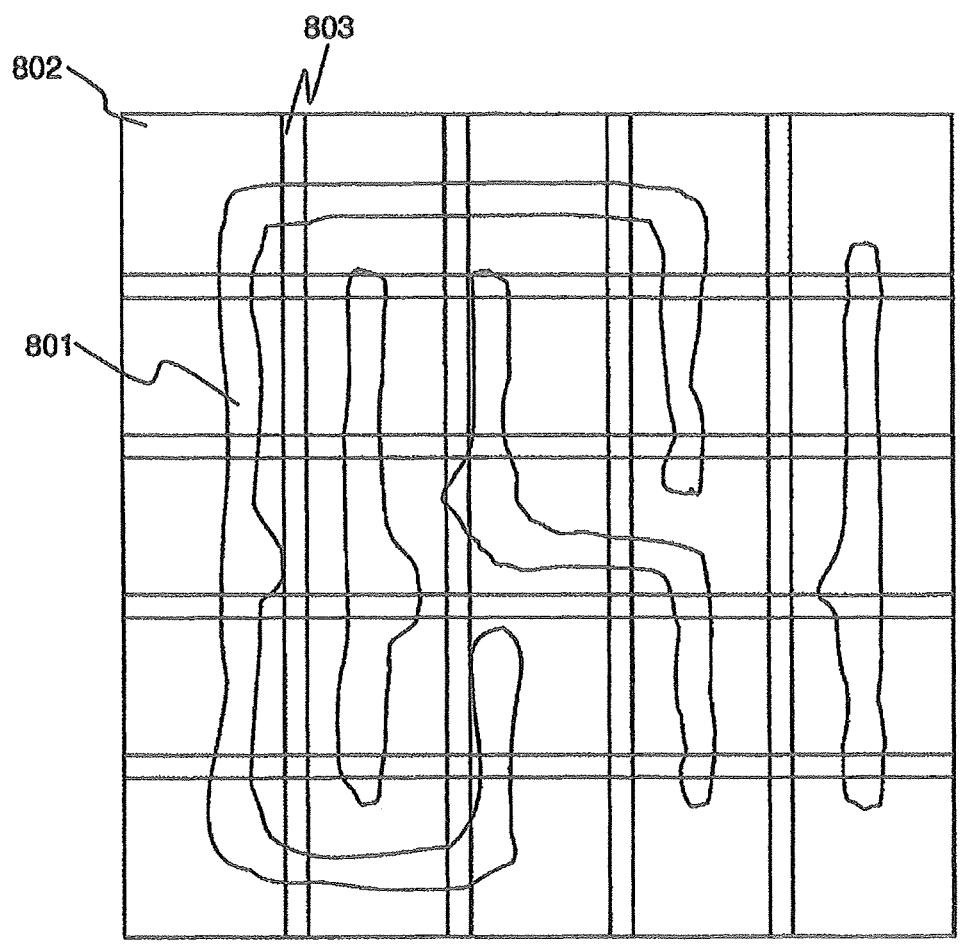
FIG. 8 is a view schematically illustrating a panorama.

Then, a technique of creating a photomask for basic elements in practice (S0003) or performing a transfer using a created photomask (S0005), taking an SEM image of the photomask or of a transferred semiconductor wafer (S0004, S0007), and creating a template library based on the SEM image is described.

Where a template library is created after an image is taken by SEM, the contour line of the pattern is extracted based on the obtained image (S0008). Various techniques can be applied other than the technique exemplified in FIGS. 3 and 4 to extract the contour line. The pattern image turned into the contour line is subjected to processing for making a panorama according to the need (S0009). The processing for creating a panorama is necessary for managing the layout data for each step for each individual basic element. This processing is applied in a case where a region expressing the whole basic element and a region in which a contour line is formed are different in size. FIG. 8 is a view schematically showing the processing for creating a panorama.

A pattern 801 in the form of a contour line expressing the whole basic element in some step is formed by combining plural fields of view 802 (in the case of the present example, 5×5 fields of view are combined). By creating a template library for each basic element, any arbitrary region can be read out according to the necessity of template creation. More accurate overlapping can be performed by forming an overlap region 803 for synthesis of images and performing pattern matching utilizing a pattern formed across two fields of view.

Processing for converting data about the contour line in the form of a panorama into a given format (e.g., GDS format) (S0010) is then performed. At this time, layer identification information, manufacturing steps, coordinate information about the contour line, and so on are also registered. Then, if the original SEM image is a mask image, a post-transfer simulation is performed on the basis of the mask image (S0011).

Information about the steps (layers) created as described so far is added, and a library is created (S0012). A summary of the library is given later.

In the present example, an image of a pattern shape (mask shape or a pattern shape on silicon (semiconductor wafer)) is previously obtained for each basic circuit. The contour line of the pattern is then extracted from the image. The shape is correlated for each basic circuit and saved as a library for pattern matching. The corresponding basic circuit is recognized from design data of the position measured when a circuit is fabricated as an actual product. The contour line is used as a template for matching for image acquisition.

In particular, for the template library for matching, each part of the pattern is taken as an SEM image at a high magnification (e.g. 200,000×) for each basic circuit. Adjacent parts are turned into a panorama so that the basic circuit is reconstructed as a high-magnification image. Subsequently, an edge is extracted from the reconstructed image for each pixel at a subpixel computational accuracy by a metrology algorithm used in metrology SEM. The contours of these edge points are extracted. Thus, the contour shape of the circuit pattern is created. This is diagrammed, for example, in the GDS2 format that is a format of design data, built into a library, and managed.

The above-described steps are carried out for all of the basic circuits constituting a semiconductor, whereby the data can be managed as a diagrammed pattern library. Pattern matching for measurements can be performed quite accurately by using the pattern library of contour lines for pattern recognition during measurements.

Since the present pattern library is obtained by diagramming patter images at an accuracy of high magnification, a shape (enlarged and reduced) arbitrarily corresponding to the magnification used during measurements can be expressed. Consequently, the magnification at which an image used for a measurement is derived can be set at will.

As described previously, edges are detected at the subpixel accuracy, and the edge points are used as coordinates constituting a graphical figure. Therefore, graphical figures can be represented at quite highly accurate resolution. If enlargement or reducing processing is performed for creation of a template, the accuracy is prevented from being impaired.

Accordingly, the template library can be used as a template creating means for addressing at relatively low magnifications (e.g., 10,000×) and also as a template means at relatively high magnifications (e.g., 200,000×) when measurements are made.

The aforementioned template library makes it possible to standardize templates used when patterns which might variously vary in size and shape such as at locations where a pattern defect might occur, known as hot spots, are subjected to pattern recognition. Therefore, a flexible work for creating recipes and stability of measurements can be accomplished.

In the technique consisting of obtaining a mask image via S0004 of FIG. 5 and creating a template library on the basis of the mask image, the contour lines of masks corresponding to basic circuits are extracted (S0008) based on the obtained mask image, and the contour lines are turned into a panorama (S0009). Data about the contour lines in the form of a panorama is converted into a given format (S0010). Then, the transferred image is simulated (S0011). Consequently, a post-transfer pattern shape can be forecasted. One example of simulation is OPC (optical proximity correction) simulation. A simulation capable of forecasting a post-transfer shape under the condition where an OPC pattern is added is applied.

Such simulations often result in cumbersome settings of various conditions under which a forecast is made. Furthermore, long computation times are often required. However, once conditions are set and a simulated shape is found, if exposure machine conditions such as the amount of exposure and dose vary, the forecasted shape can be corrected relatively easily simply by modifying the conditions.

Stability of image acquisition can be accomplished by registering forecasted transfer shapes corresponding to basic circuits found by the above-described means as a template library (S0012) and using them during creation of templates for matching.

This technique is a means that can easily cope with variations in conditions of the exposure machine, process conditions, or the like. Therefore, this technique can be used together with the technique of using the aforementioned mask shapes and contour lines of transferred shapes of silicon directly as templates for matching.

Use of the present technique of forecasting a transferred shape using a simulation has the object of further enhancing the stability of measurements. In addition, the technique can be used as an index in managing patterns during manufacturing steps by measuring the difference between the forecasted shape and the actually transferred shape. When a mask image is acquired, if an imaging recipe for a scanning electron microscope for photomasks is previously created, efficient measurements are enabled. In this case, panoramic image taking positions for basic circuits and imaging magnification are set in the recipe. Further, in template library creating steps which pass through (S0005) to (S0007) of FIG. 5, a library is created on the basis of an actually transferred pattern and so a template most faithful to the actual image can be created.

Figure 9:
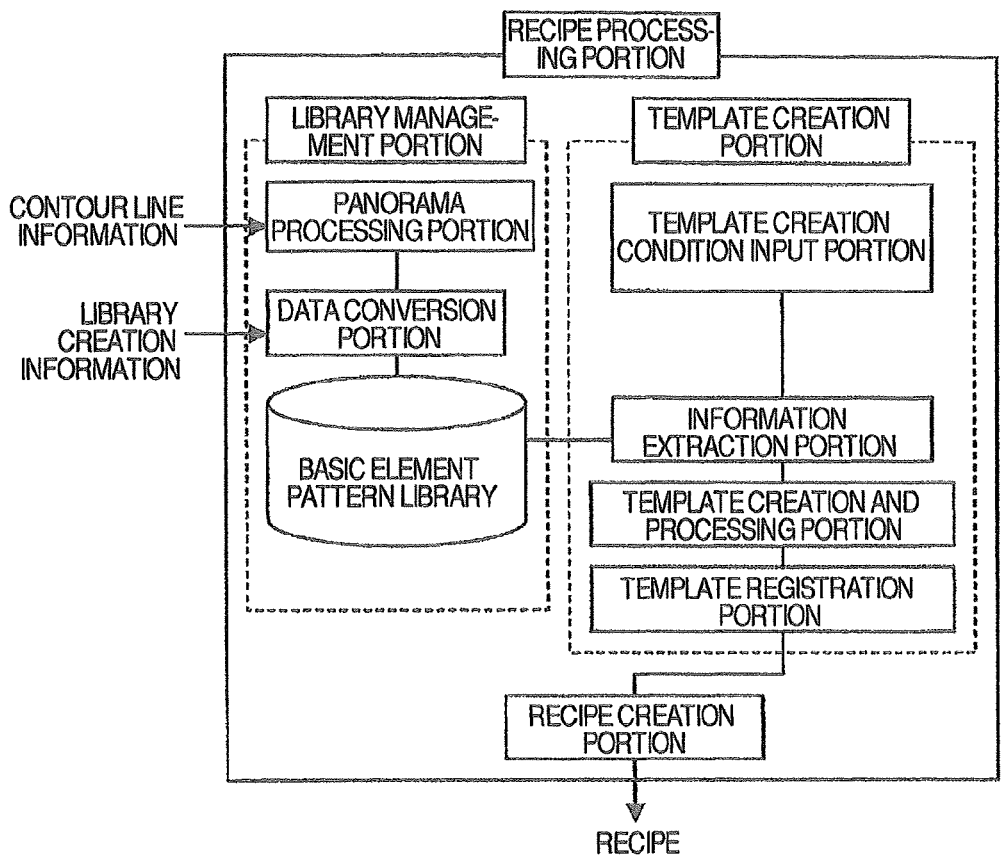
FIG. 9 is a diagram schematically illustrating a recipe processing portion having a basic element pattern library.

A recipe processing portion including the template library created through the steps as exemplified in FIG. 5 is next briefly described with reference to FIG. 9. As exemplified in FIG. 9, the recipe processing portion consists principally of a library management portion and a template creation portion. A summary thereof is as follows.

(1) Library Management Portion

The library management portion creates and saves data used to create a template for pattern matching for each basic circuit.

As described previously, it is customary that a semiconductor circuit of high integration level is composed of a combination of basic circuits that provide a basis in processing signals. During semiconductor manufacturing, preparations are made using basic circuits as standard parts for each manufacturing step (for example, 45-nm design rules) and, therefore, there is the possibility that the number of types of the circuits reach several hundreds. The preparatory work starts with performing a circuit design for each circuit. The operating characteristics of the circuits are simulated. Layouts are designed and then masks are created. Transferability on semiconductor wafers is evaluated. The circuit characteristics on semiconductor wafers are verified. During this process, if desired results are not obtained, information about circuits and layout design is modified or the manufacturing process is adjusted. The verification and adjusting work are continued until desired results are obtained.

Figure 10:
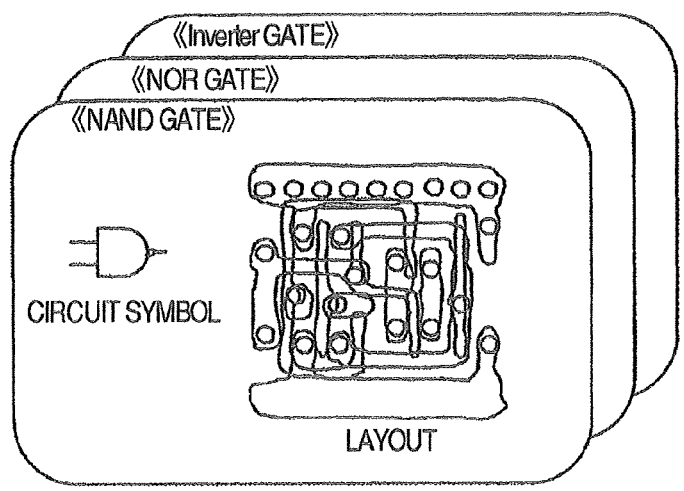
FIG. 10 is a view schematically illustrating a template library stored in the basic element pattern library.

FIG. 10 is a view schematically illustrating a template library stored in a basic element pattern library. Contour line information about transferred circuit patterns is collected in the library for each type of circuit. When contour lines are extracted, contour shapes are created using the proper layout data (e.g., GDS data). At this time, the corresponding relationship with the circuit data used in the layout design stage is used and the corresponding circuit names are attached to the graphical figures of contour lines. This expresses that the data is an assemblage of contour line data elements constituting the circuit. This processing is performed, for example, by a data conversion portion. Information about the corresponding relationship is used when a correlation with the circuit name attached to the layout of the product is taken when a recipe of product wafers is created.

Figure 15:
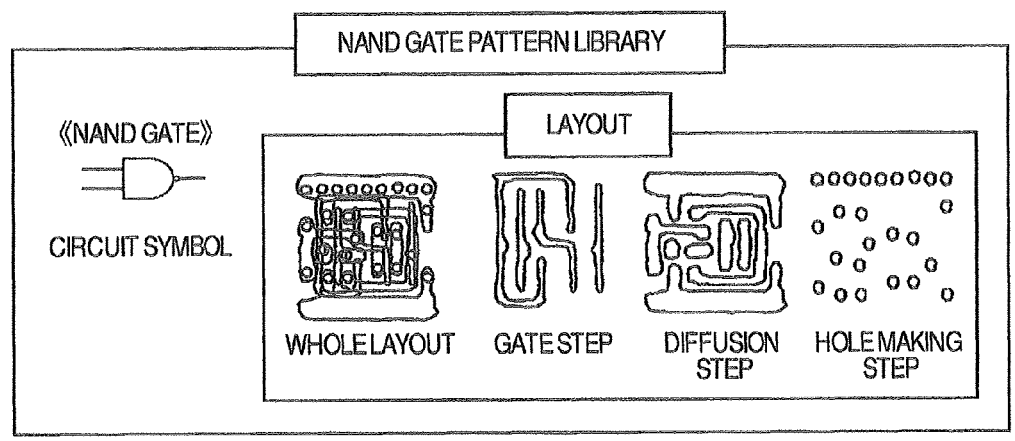
FIG. 15 is a view schematically showing a template library for a certain basic element.

For example, when a template library of NAND circuits as exemplified in FIG. 15 is created, an image of each part of the pattern forming each NAND circuit is taken at a relatively high magnification (e.g., 20,000×) and the images are combined into a panorama, thus reconstructing one circuit pattern. Then, a contour shape is extracted from the panoramic image and correlated as the contour line of the corresponding NAND circuit, and registered into the library. This processing is also performed for layers (i.e., gate layers, diffusion layers, hole layers, and so on) and registered in the library. Furthermore, similar processing for making panorama-and-contour lines is performed on every kind of basic circuit, and the results are registered in the pattern library.

In the present example, a library is created after plural images are turned into a panorama because it is used for matching templates (low magnifications) used for addressing and also for templates (high magnifications) used for measurements by taking images of various parts of each basic circuit at high magnification, turning the images into a panorama, and diagramming contour lines by GDS. When the contour lines are created, if images of one chip are used, the shape of the contour lines might not be smooth by the effects of edge roughness or the like. This may be a factor hindering the stability of matching. Accordingly, when contour lines are created, the same pattern of plural chips are used and averaged, and average contour lines may be used.

The present example realizes a stable imaging method by using a contour line of a transferred pattern. As its one example, an imaging recipe can be created using a contour line (simulated mask contour (SMC)) obtained by simulating an image to be transferred to a semiconductor wafer through the use of a contour line extracted from a mask image. Main kinds of simulation include (1) a simulation of locations of hot spots (dangerous locations in patterning), (2) a simulation of a defect correction part for a defect mask location, and (3) a simulation of a mask contour line relative to a standard cell circuit.

A method of creating a contour line extracted from a mask image is implemented similarly to the panorama processing described so far, and the results are registered in a library.

The basic element pattern library manages contour lines created by corresponding layout data about each basic circuit and by the panorama processing or the like. The library has a 1:1 corresponding relationship with the layout data and thus is bidirectionally accessible to 1) circuit information, 2) layout information, and 3) contour line information. Consequently, association with them can be traced even if a search is made from any one of the three kinds of information.

Figure 11:
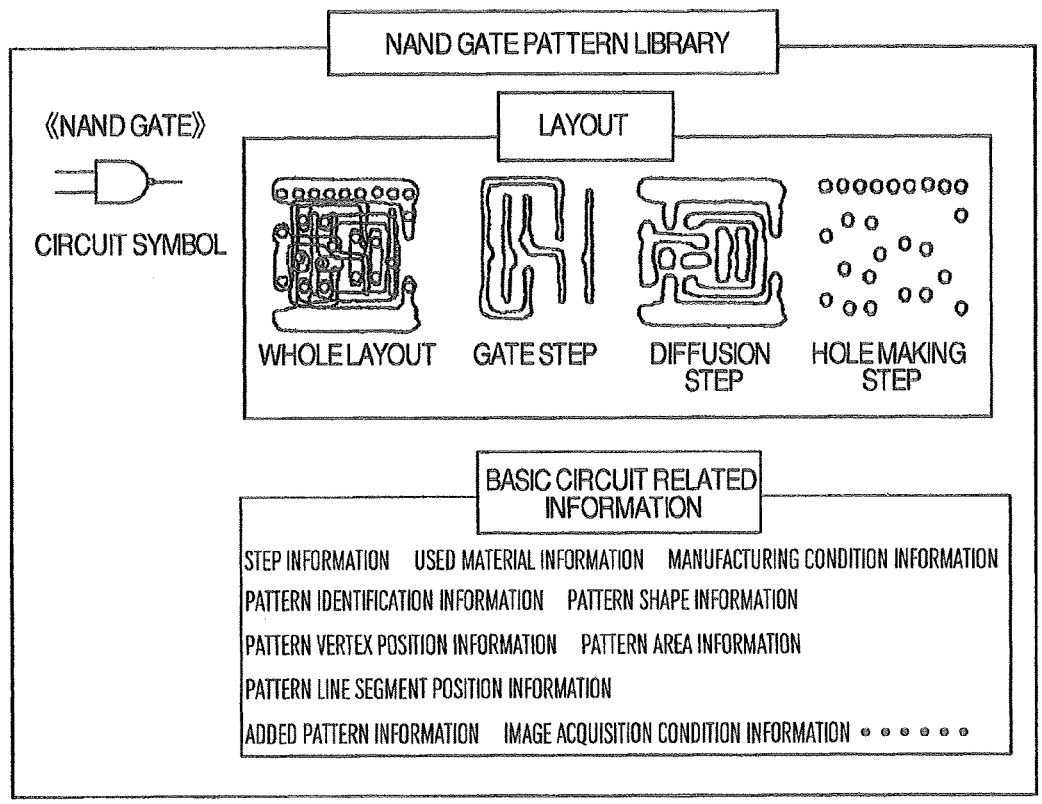
FIG. 11 is a diagram schematically illustrating a template library for a certain basic element.

Consequently, template creation conditions are specified with ease at the template creation portion described later. Furthermore, it is expected that advantageous effects will be produced when applied variously to the measurement portion. In addition, requisite information can be selected on the basis of more detailed template creation conditions by registering other information related to the basic circuit as exemplified in FIG. 11 in the library as well as the layout information and making layout information having the related information extractable by specifying information.

Figure 7:
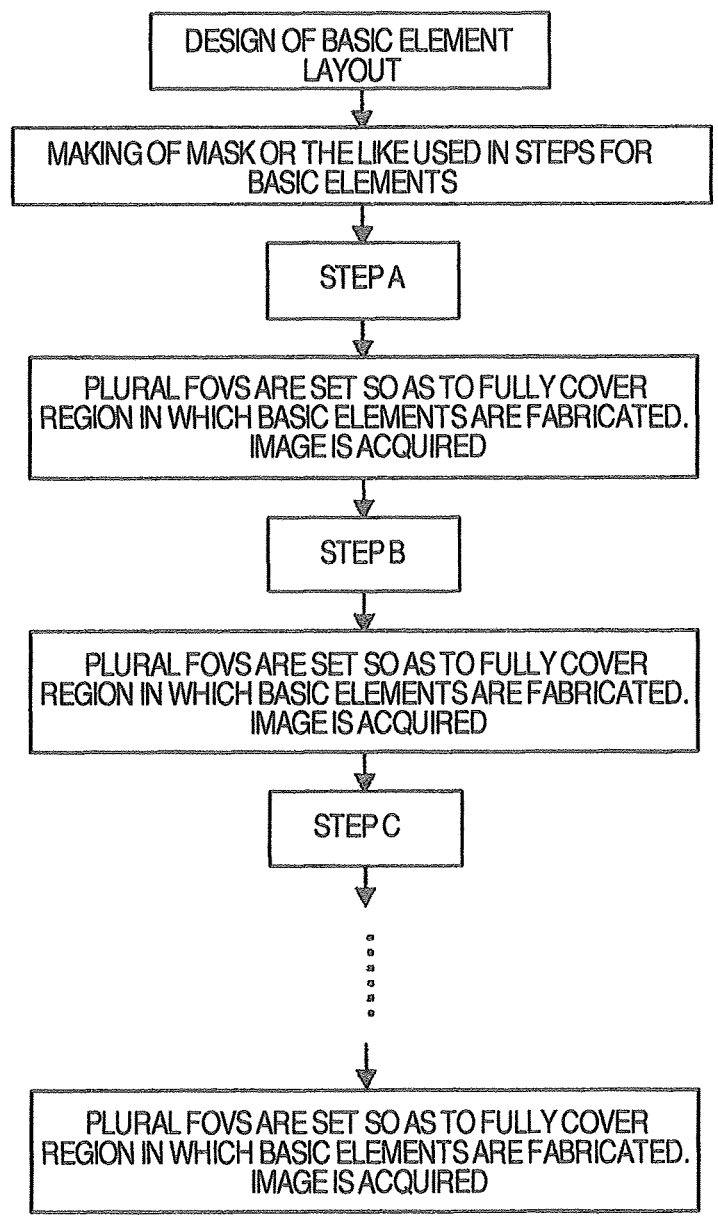
FIG. 7 is a flowchart illustrating steps for obtaining images required to create a template library.

FIG. 7 is a flowchart illustrating steps of creating a template library during a transfer step of basic elements. Information necessary for the library is collected by performing panorama processing based on acquisition of plural fields of view (FOVs) whenever a layer is formed. Since the template library for the creation of a library can be created based on the designs of basic elements, the library for creation of the library can be built aside from steps for mass-producing wafers.

(2) Template Creating Portion (Recipe Creating Portion)

Figure 6:
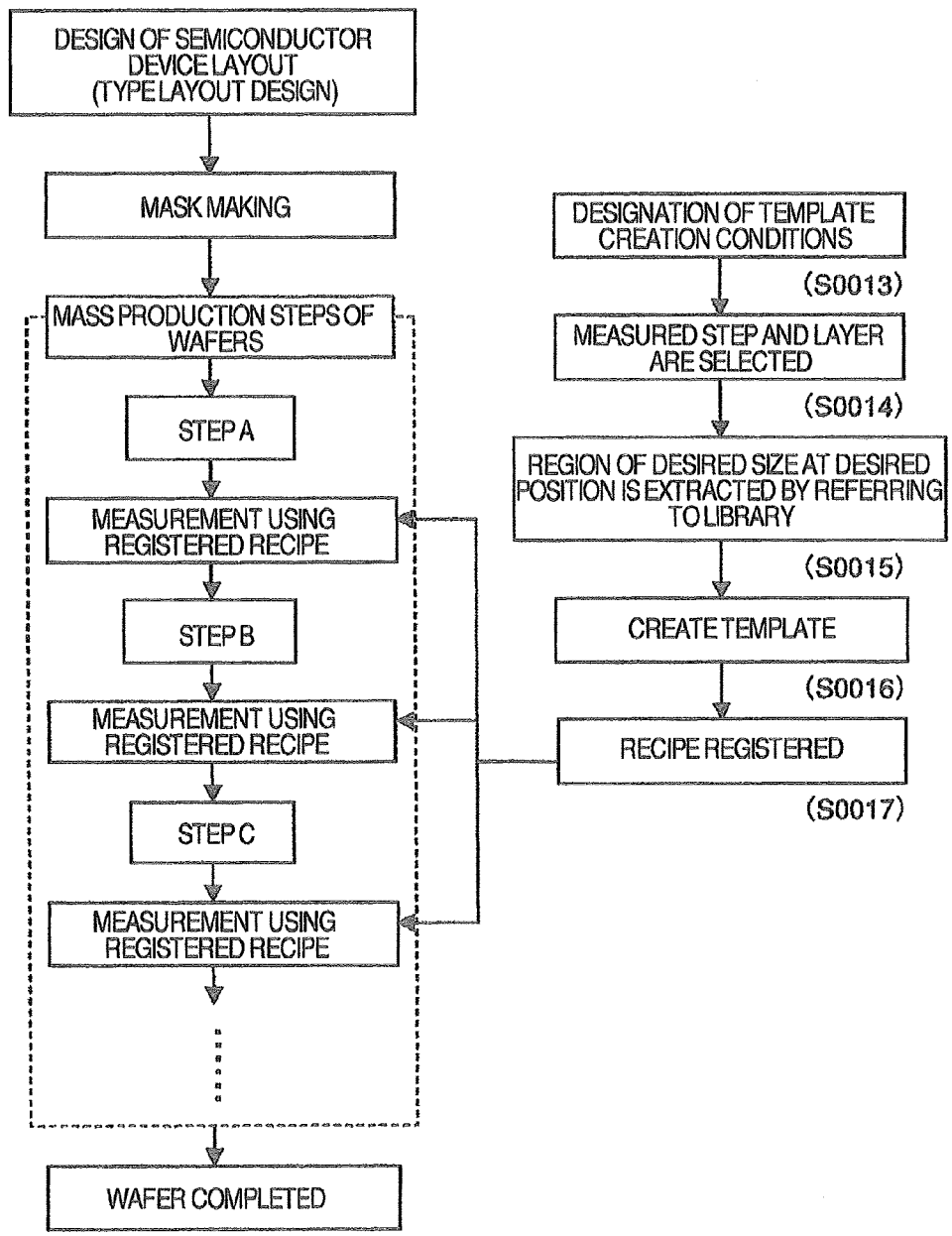
FIG. 6 is a flowchart illustrating steps for creating a template using the template library.

The template creating portion creates templates and registers them into a recipe. A process of creating a recipe on the basis of template creation is exemplified in FIG. 6.

First, as one of template creation conditions, the position of a subject to be measured or of a template is specified in terms of layout data (S0013). Then, a basic circuit is identified from circuit information of a position corresponding to specified coordinates indicated by the layout data, and a corresponding pattern library is determined (S0014). At this time, the layer of the pattern is determined from the layer information to be measured. The position of contour line data corresponding to the determined pattern library is found, and the imaged range is calculated on the basis of a field of view region indicated by a measurement magnification (S0015). Contour line information (pattern information) contained in the region is extracted from the pattern library and then a matching template for measurements is created (S0016) and registered as a recipe (S0017).

In the present example, if design information about the basic circuits or transfer information about the basic circuits is available, it is possible to create a template used for mass production steps. A measurement recipe can be quickly created either before or after the mass production.

Figure 14:
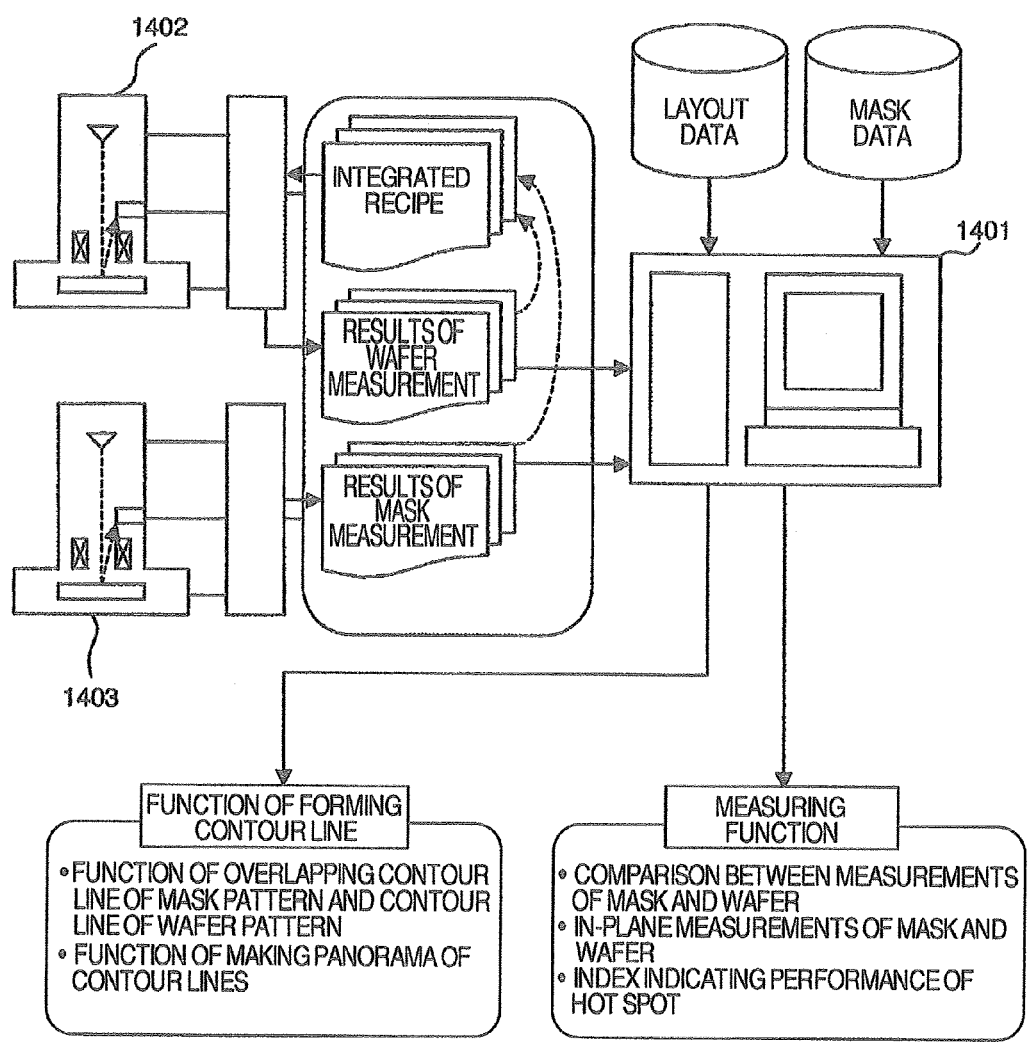
FIG. 14 is a view schematically showing a composite system including plural measuring instruments.

A measurement system capable of creating various libraries exemplified in FIG. 5 and a measurement recipe based on the libraries is schematically shown in FIG. 14. ACD-SEM 1402 is an SEM for semiconductor wafers. ACD-SEM 1403 is an SEM for photomasks. A data management unit 1401 is used to form a recipe on the basis of layout data and mask data. The data management unit 1401 extracts a contour line based on a mask image acquired by the CD-SEM 1403 and creates a measurement recipe for the CD-SEM 1402 based on the results.

The system configuration described so far makes it possible to manage all the recipe information about the two CD-SEMs and to share the recipes.

In particular, corresponding positions of a photomask and a semiconductor wafer can be managed using identification information (such as the same ID number), and their mutual coordinate systems can be correlated with each other using the ID.

Generally, photomasks and semiconductor wafers are different in scale. The ID permits scale conversion coefficients to be calculated indiscriminately and so measurement results can be analyzed in an interlocking manner unconsciously of scale.

Consequently, recipes are integrated. In addition, measurement results can be displayed on one GUI. Therefore, the results of measurements of masks and the results of measurements of silicon can be displayed in an interlocking manner.

As described previously, by creating recipes for pattern matching off-line without using any CD-SEM, automation can be promoted and labor saving can be achieved. Furthermore, prior to the end of manufacture either of a wafer to be measured or of a mask plate, a recipe for measurement can be created in advance and so time loss can be eliminated in starting the measurement.

A matching template quite close in shape to a pattern formed either on a wafer to be measured or a mask plate can be used and, therefore, quite high robustness can be accomplished during measurements. Furthermore, the inventive technique can be used also for detection of abnormal pattern shapes wherein a template is used as a reference.

Where layout information stored in the aforementioned template library has been created based on imaging of a semiconductor wafer, a library of basic circuits that are considered to be arranged in large quantities on a sample can be created simply by selectively taking SEM images of the basic circuits. Therefore, a template based on an SEM image quite close to the actual image can be created efficiently. Also, where layout information stored in the template library has been created on the basis of a simulation based on layout data, mask data, or mask image, the library can be created prior to designing of a semiconductor layout or manufacturing steps. Hence, a template can be quickly created before or after an actual wafer is fabricated. Furthermore, it suffices to perform a partial simulation of basic circuits. Therefore, it is expected that the efficiency of the simulation will be enhanced.

REFERENCE SIGNS LIST

101: data management unit
102, 103: SEMs
104, 105, 110: controllers
106, 107: communication lines
108: simulator
109: focused ion beam instrument
201: electron source
202: extraction electrode
203: electron beam
204: condenser lens
205: scan deflector
206: objective lens
207: sample chamber
208: sample stage
209: sample
210: electrons
211: secondary electrons
212: conversion electrode
213: detector

The invention claimed is:

1. A method of creating a template for performing template matching with a pattern on a semiconductor device, said method comprising the steps of:
specifying positional information and layer information about the semiconductor device;
extracting contour line data regarding the specified position and layer on the basis of the specified positional information and layer information from a library which stores contour line data, obtained in accordance with a scanning electron microscope image or simulation, of a plurality of layers for each one of a plurality of logic circuits present on the semiconductor device; and
registering the extracted contour line data of a part of one of the logic circuits as the template.

2. The method of creating a template of claim 1,
wherein data created on the basis of irradiation of the logic circuits with a charged particle beam, layout data about the logic circuits, mask data, or data created on the basis of irradiation of the mask formed based on the mask data with a charged particle beam are stored in said library.

3. The method of creating a template of claim 2,
wherein the data created on the basis of irradiation of said logic circuits or said mask with the charged particle beam are contour line data obtained by extracting contour lines of images formed based on said irradiation by the charged particle beam.

4. The method of creating a template of claim 3,
wherein the data created on the basis of irradiation of said logic circuits or said mask with the charged particle beam have been obtained by combining said contour line data so as to fully cover a region in which said logic circuits are formed.

5. A template creating device for creating a template for performing template matching with a pattern on a semiconductor device, said template creating device comprising:
a condition input portion for specifying positional information and layer information about the semiconductor device;
a storage medium storing a library in which contour line data, obtained in accordance with a scanning electron microscope image or simulation, of a plurality of layers for each one of a plurality of logic circuits present on the semiconductor device is stored; and
a processing portion for extracting contour line data of a part of one of the logic circuits from the library on the basis of the positional information and layer information entered from the condition input device and for creating the template on the basis of the extracted contour line data.

6. The template creating device of claim 5,
wherein data created on the basis of irradiation of the logic circuits with a charged particle beam, layout data about the logic circuits, mask data, or data created on the basis of irradiation of the mask formed based on the mask data with a charged particle beam are stored in said library.

7. The template creating device of claim 6,
wherein the data created on the basis of irradiation of said logic circuits or said mask with the charged particle beam are contour line data obtained by extracting contour lines of images formed based on the irradiation by the charged particle beam.

8. The template creating device of claim 7,
wherein the data created on the basis of irradiation of said logic circuits or said mask with the charged particle beam have been obtained by combining said contour line data so as to fully cover a region in which said logic circuits are formed.

9. A non-transitory computer readable medium storing a computer program executed by a computer connected with a charged particle beam instrument to create a template for performing template matching with a pattern formed on a sample, the charged particle beam instrument being operable to form an image by scanning a charged particle beam over the sample, said computer program performing the steps of steps of:
causing the computer to extract, on the basis of a designation of positional information and layer information about the sample, contour line data regarding the specified position and layer from a library storing contour line data, obtained in accordance with a scanning electron microscope image or simulation, of a plurality of layers for each one of a plurality of logic circuits present on the semiconductor device; and registering the extracted contour line data of a part of one of the logic circuits regarding the specified position and layer as the template.

10. The non-transitory computer readable medium storing the computer program of claim 9, wherein data created on the basis of irradiation of the logic circuits with the charged particle beam, layout data about the logic circuits, mask data, or data created on the basis of irradiation of the mask formed based on the mask data with the charged particle beam are stored in said library.

11. The non-transitory computer readable medium storing the computer program of claim 10, wherein the data created on the basis of irradiation of said logic circuits or said mask with the charged particle beam are contour line data obtained by extracting contour lines of images formed based on the irradiation by the charged particle beam.

12. The non-transitory computer readable medium storing the computer program of claim 11, wherein the data created on the basis of irradiation of said logic circuits or said mask with the charged particle beam have been obtained by combining said contour line data so as to fully cover a region in which said logic circuits are formed.

\* \* \* \* \*